United States Patent [19]
Carr et al.

[11] Patent Number: 5,222,487
[45] Date of Patent: * Jun. 29, 1993

[54] HINGED TRACHEOSTOMY TUBE OBTURATOR

[75] Inventors: Ian R. Carr, Jaffrey, N.H.; Denis LaBombard, Georgetown, Mass.

[73] Assignee: Smiths Industries Medical Systems, Inc., Keene, N.H.

[*] Notice: The portion of the term of this patent subsequent to Aug. 27, 2008 has been disclaimed.

[21] Appl. No.: 717,828

[22] Filed: Jun. 21, 1991

Related U.S. Application Data

[63] Continuation-in-part of Ser. No. 492,406, Mar. 8, 1990, Pat. No. 5,042,475, which is a continuation of Ser. No. 252,099, Sep. 30, 1988, abandoned.

[51] Int. Cl.$^5$ ............................................. A61M 16/00
[52] U.S. Cl. ............................ 128/200.26; 128/207.14
[58] Field of Search ...................... 128/200.26, 207.14, 128/207.15; 600/12

[56] References Cited

U.S. PATENT DOCUMENTS

| | | | |
|---|---|---|---|
| 3,794,041 | 2/1974 | Frei et al. ............................. | 600/12 |
| 4,231,365 | 11/1980 | Scarberry ........................ | 128/207.15 |
| 5,042,475 | 8/1991 | LaBombard ................... | 128/200.26 |

Primary Examiner—Edgar S. Burr
Assistant Examiner—Aaron J. Lewis
Attorney, Agent, or Firm—Pollock, Vande Sande & Priddy

[57] ABSTRACT

In combination, a tracheostomy tube including a curved cannula lying substantially within a given plane and formed with a non-constant radius, and an obturator means insertable into the cannula for guiding intubation of the tracheostomy tube into the cannula. The obturator comprises a single piece member formed of a resilient and flexible material and curvable upon insertion within the cannula with a non-constant radius lying within the given plane, the member having proximal and distal ends and a shaft extending therebetween, the shaft over a substantial portion of its length being dimensioned such as to impart sufficient rigidity both in the direction substantially perpendicular and also substantially parallel to the given plane. The shaft also includes a first flexible portion being of substantially rectangular cross-section having a width and a thickness, the width as measured perpendicular to the given plane substantially exceeding its thickness. The shaft at the flexible portion is easily flexible along its length in the given plane of its curvature but is substantially stiff in a direction perpendicular to the given plane because of the greater width of its cross-section.

6 Claims, 3 Drawing Sheets

HINGED TRACHEOSTOMY TUBE OBTURATOR

This application is a continuation-in-part of application Ser. No. 07/492,406 filed on Mar. 8, 1990 now U.S. Pat. No. 5,042,475, which is a continuation of application Ser. No. 252,099 filed on Sep. 30, 1988, now abandoned.

FIELD OF THE INVENTION

The present invention relates to tracheostomy tube devices and more particularly to an improvement in guiding devices such as obturators that are used to assist in the insertion of a tracheostomy tube into a patient's trachea.

The obturator of the present invention is particularly designed for use with a tracheostomy tube which includes a non-constant radius cannula as a part of its configuration.

BACKGROUND OF THE INVENTION

Tracheostomy tubes are widely used to supply air to the lungs of unconscious patients such as injured persons and patients undergoing surgery.

In order for the tracheostomy tube to function as intended it must be properly applied to the trachea so that air can be directed through the tube and into the trachea. However, proper insertion of the tube represents a very difficult task and it is possible during the insertion procedure to miss the surgically prepared opening in the trachea and misguide the tracheostomy tube device into the surrounding tissue. Failure to properly insert the tracheal tube can cause serious problems and incur dangerous consequences for the patient. Otolaryngologists, Thoracic Surgeons, General Surgeons and other clinical professionals may experience difficulties in performing intubation procedures. To assist the physician, a variety of guides such as stylets or obturators are available to clinicians to guide and to assist the placement of such tubes in the patient's trachea.

The obturators are used to guide metal or polymeric tracheostomy tubes such as described, for example, in U.S. Pat. Nos. 3,088,466 and 3,659,612 to Shiley et al. The characteristic common feature of these tubes is a constant radius design of the cannula portion. A constant radius cannula is defined herein as a cannula having a continuous curvature between its proximal and distal ends.

It is important in the intubation procedure that the obturator be not only easily insertable into the cannula, but also easily and safely removable after the intubating has been completed.

The removal of the obturator used with tracheostomy tubes having constant radius cannula does not present significant problems as the obturator can be easily pulled along the radius of curvature for easy frictionless removal.

However, many flexible tracheostomy tubes used nowadays are designed to include a non-constant radius cannula. Typically such a tracheostomy tube has at least two substantially straight cannula sections and a curved section located therebetween. The arc of the curve may be designed as forming a right angle or approaching a right angle. The straight sections may be of considerable length. The withdrawal of the obturator from the non-constant radius cannula presents a more difficult task.

U.S. Pat. No. 4,471,776 to Cox describes an example of a tracheostomy tube including an obturator with an adjustable shape. This obturator includes a mealable shaft which allows for the obturator placed inside the tube to be bent together with the tube to a desired curved configuration. However, it is difficult to remove the obturator from the tracheostomy tube since the forces which maintain the curved geometry of the tube and the obturator have to be overcome.

Other types of flexible guiding devices available on the market are so-called "steerable" wire guide devices which bend to a selected fixed constant curvature. Such guiding stylets inserted into the catheter/cannula are designed to impact the curvature to the catheter/cannula. The wire-type guiding devices are most commonly employed with medical devices having an extremely long length as compared to their diameter which is usually very small. The spring-like functions of such small diameter guidewires would be difficult to overcome when such mechanisms are applied to the typical geometry of a tracheostomy or endotracheal tube.

For accomplishing a proper intubation, it is very important that the cannula maintains its shape and does not become occluded or distorted, such that an airway passway is maintained clear through the intubated cannula during and after the intubation procedure.

There is a significant need in the art for an obturator suitable for use with tracheostomy tubes, particularly those including a non-constant radius cannula, which would eliminate disadvantages of the prior art. There does not exist a highly flexible, plastic, single-piece, easily insertable and safely removable guiding device especially suitable for tracheostomy tubes having non-constant radius cannula.

There is a need for an obturator which would substantially prevent tracheostomy tube occlusion or collapse during the intubation and additional distortion of the device once the tube is in place in the trachea, increasing the patient's safety and comfort.

SUMMARY OF THE INVENTION

It is the primary object of the present invention to provide an improved device which assists in guiding a tracheostomy tube towards the incision made in the trachea in order to facilitate proper insertion of the tube.

Another object of the present invention is to provide an obturator which is especially suitable for use with tracheostomy tubes which include a non-constant radius cannula.

A further object of the present invention is to provide an obturator which can be easily inserted and safely removed through straight and curved portions of the non-constant radius cannula.

Another object of the present invention is to provide an obturator which is highly flexible, but able to maintain the geometry of the cannula during the intubation procedure to prevent occlusion, collapse and distortion of the cannula, and to ensure an internal non-disturbed airway.

Still another object of the present invention is to provide an obturator which is highly flexible and will easily assume the preferred contour of the tracheostomy tube, and will maintain the internal geometry of the cannula during intubation.

Another object of the present invention is to provide a multi-component highly flexible obturator made as an integral, single piece member thereby eliminating possible failure of assembly points and enhancing safety of the device.

Still another object of the present invention is to provide a plastic obturator which has a simple structure and is inexpensive to manufacture.

The above and other objects of the present invention are accomplished by a structure of the obturator for use in intubating tracheostomy tubes into a patient's trachea which includes a single-piece, flexible member having a distal end and a proximal end and a shaft means extending therebetween. The shaft means is comprised of a substantially flat strip member and a plurality of segments substantially perpendicular to the flat strip member. The flat strip forms a plurality of hinged portions alternating with the plurality of segments. The flexible member has a grasping means formed at its proximal end and a tip member provided at its distal end. The tip member has a bullet-like conical shape. A smooth transition zone is formed between the tip member and the outer diameter of the tracheostomy tube.

In the preferred embodiment of the present invention, the single-piece, flexible obturator is made of polymeric material and the plurality of segments (protuberances) are dimensioned such as to substantially correspond to the inner diameter of the cannula.

The present invention due to its structure and nature of the material, flexes easily at the hinged portions in the axis of the curved tube portion when it is being inserted or removed from the tracheostomy tube without applying forces which can cause changes in the cannula's shape. At the same time, when placed within the tube, the obturator substantially fills, with the plurality of segments, the interior of the cannula whereby maintaining geometry of the tube during the intubation. This, in turn, prevents occlusion or collapse of the tube during intubation and any distortion of the tube once in place in the patient's trachea, and ensures a non-disturbed airway through the tracheostomy tube device.

The structure of the present invention obturator is substantially resistant to compression forces, which typically in mealable wire-type stylet obturators or strap-like plastic current state of the art devices, because they do not fill the cannula completely, allow the obturator tip to push back and complicate the intubating procedure due to the lack of a smooth transition from the obturator tip to the tracheostomy tube outside the diameter. The smooth transition is therefore secured between the tip member of the obturator and the outer diameter of the tracheostomy tube device to the present invention structure.

The single-piece obturator structure also increases the reliability of the tracheostomy tube assembly by eliminating additional possible failure points common to all devices of multicomponent configuration, an enhanced safety feature for both the clinician and the patient during intubation procedure.

Additional key features of the preferred embodiment of the present invention include a multi-geometry highly flexible single piece structure and polymeric material construction, resulting in a device that provides easier, more efficient and safer use during the intubation procedure increasing patient safety and comfort.

In another preferred embodiment of the present invention means are provided in the structure of the flexible obturator which prevent the tip of the obturator from being pushed up inside the tracheostomy tube, while the physician is placing the tube into the patient.

Other advantages achievable by the present invention will become apparent from the following description of the preferred embodiment of the present invention with reference being made to the accompanying drawings.

DETAILED DESCRIPTION OF THE PREFERRED EMBODIMENT(S)

Figure 1:
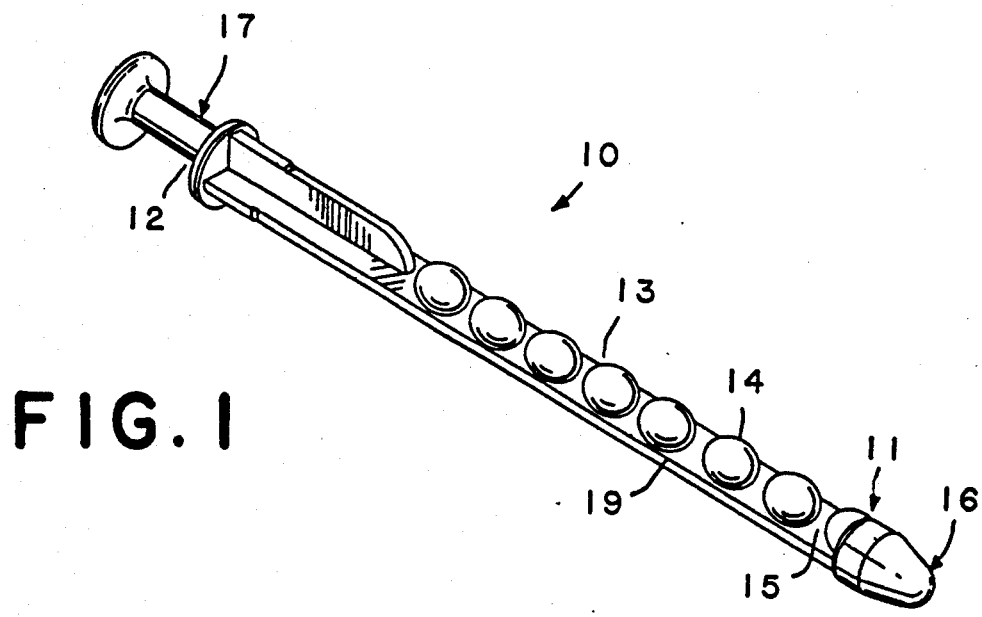
FIG. 1: shows a perspective view of the first preferred embodiment of the present invention obturator.
Figure 2:
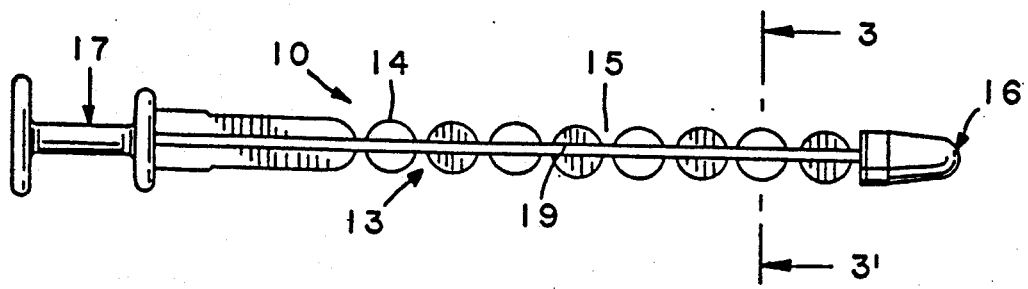
FIG. 2: shows a side view of the embodiment of FIG. 1.
Figure 3:
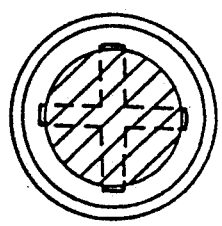
FIG. 3: shows a cross-section of the first embodiment of the present invention obturator taken along lines 3'—3' in FIG. 2.

Referring first to FIGS. 1 and 2, an obturator 10 is shown, which includes a single-piece member having a distal end 11, proximal end 12 and a shaft means 13 extending between the distal and proximal ends 11,12. The shaft means 13 is comprised of a substantially flat member 19 having a rectangular cross-section and having a plurality of segments or protuberances 14 disposed substantially perpendicular to the flat strip member 19. The rectangular cross-section of the shaft means has a width and a thickness with the width substantially exceeding its thickness. This flat strip member 19 forms a plurality of hinged portions (or spaces) 15 alternating with the segments 14. In the preferred embodiment shown in FIGS. 1-4, the segments 14 are bead-like shaped. The obturator 10 includes a grasping means 17 formed at its proximal end 12, and a tip member 16 provided at its distal end 11. In the preferred embodiment, the obturator 10 is made as an integral, plastic, single-piece device.

Figure 4:
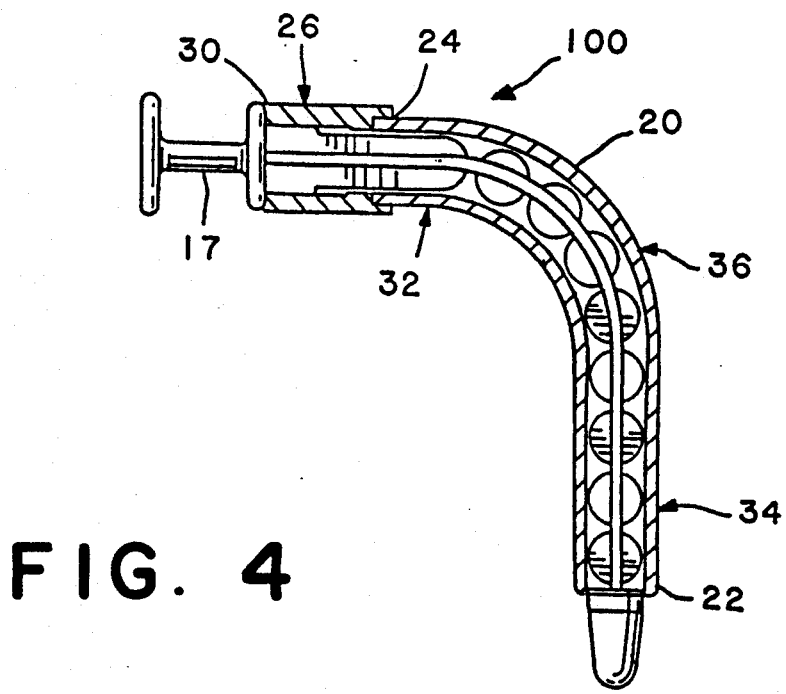
FIG. 4: shows a cross-section view of a non-constant radius tracheostomy tube with the obturator according to the present invention placed inside the tube.
Figure 7:
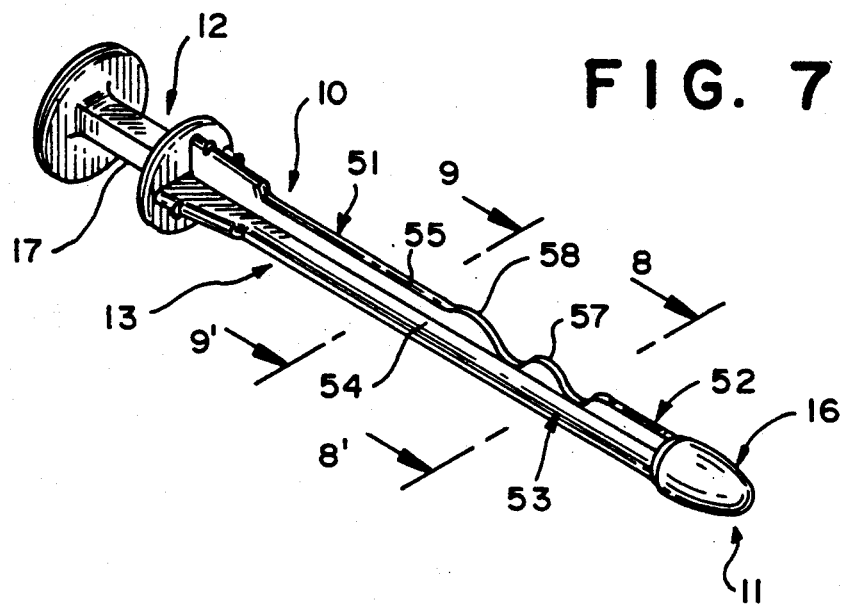
FIG. 7: shows a perspective view of the third preferred embodiment of the present invention obturator.
Figure 9:
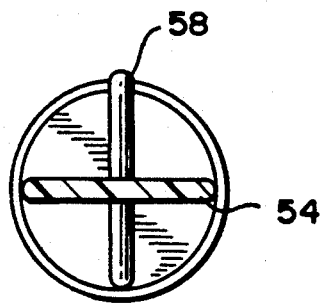
FIG. 9: shows a cross-sectional view of the embodiment of FIG. 7 taken along lines 9—9'.
Figure 8:
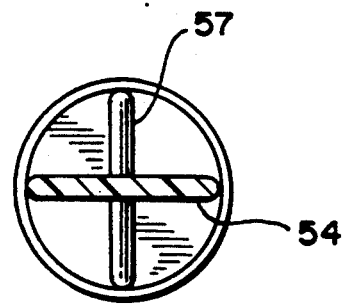
FIG. 8: shows a cross-section view of the embodiment of FIG. 7 taken along lines 8—8'.
Figure 10:
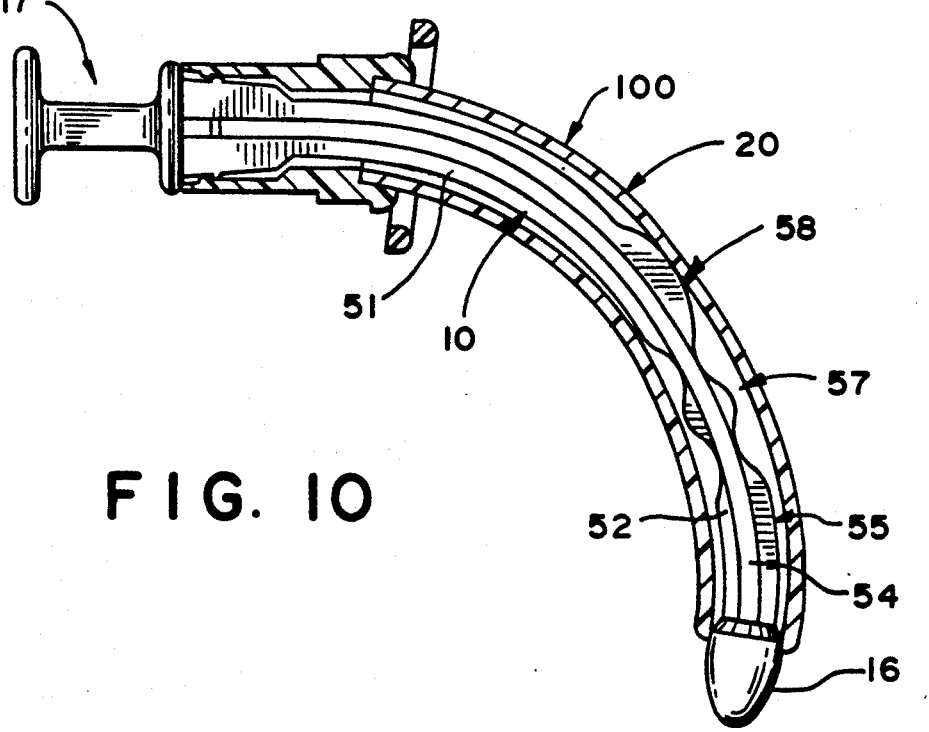
FIG. 10 shows a cross-sectional view of a non-constant radius tracheostomy tube with the obturator according to the third embodiment of the present invention inserted therein.

FIG. 4 shows tracheostomy tube 100 including a non-constant radius curved cannula 20 lying substantially within a given plane and having straight portions 32 and 34 and curved portion 36 located therebetween. The cannula 20 includes a proximal end 24 and a distal end 22. A connector 26 is connected to the proximal end 24 of the straight portion 32. In FIG. 4, the obturator 10 for use in intubating the tracheostomy tube 100 into the patient's trachea is shown in place within the tracheostomy tube 100.

As clearly shown in FIG. 4, the obturator shaft means 13 flexes at the hinged portions 15 in the axis of the curved cannula portion 36. The grasping means 17 forming in the preferred embodiment, a handle projects beyond the end 30 of the connector 26. The tip member 16 of the obturator 10 projects beyond the end 22 of the cannula 20. The tip member 16 has a bullet-like conical shape which facilitates the guiding of the tracheostomy tube during the intubating procedure. As is clearly apparent from FIGS. 3 and 4, the diameters of the plurality of segments 14, substantially corresponds to the inner diameter of the cannula 20. Therefore, when placed within the tube, the obturator substantially spans the interior of the cannula 20 which allows it to maintain the shape of the tube during the intubation.

Such a structure of the obturator is very advantageous, since it substantially prevents occlusion or collapse and distortion of the tracheostomy tube, and ensures the existence of a non-disturbed airway.

Figure 6:
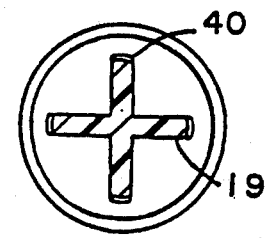
FIG. 6: shows a cross-section view of the embodiment of FIG. 5.
Figure 5:
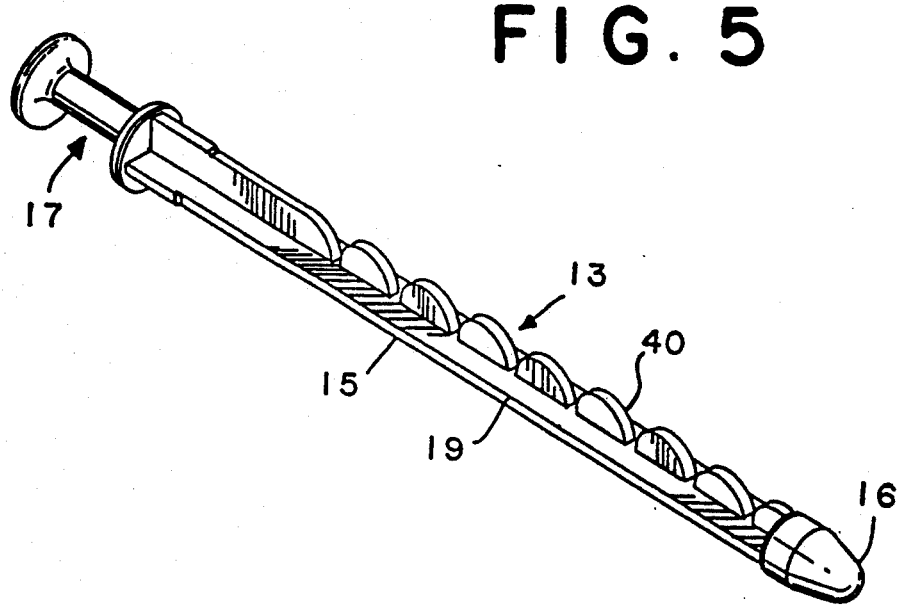
FIG. 5: shows a perspective view of the second preferred embodiment of the present invention obturator.

FIGS. 5 and 6 show another embodiment of the present invention in which the shaft 13 is comprised of a plurality of substantially flat disc-like circular segments 40 which are substantially perpendicular to the hinged portions 15 of the strip member 19. The diameter of circular segments 40 also substantially corresponds to the inner diameter of the cannula 20.

Other shapes for a plurality of segments can be envisioned, for example, having a trapezoidal configuration.

According to the preferred embodiment, the obturator 10 is made of a polymeric material, such as for example polyolefins. However, other plastic materials can be used which are suitable for a multi-hinged geometry.

Due to the multi-hinged structure and the nature of the plastic material, the obturator 10 easily flexes only in the radial direction of the cannula 20 in the axis of the curved tube portion 36, whereby it is easily insertable and removable from the tracheostomy tube 100. These features of the present invention are particularly important and advantageous during the withdrawal of the obturator from the non-constant radius cannula, because the forces necessary for the withdrawal of the obturator from the cannula are substantially decreased.

Also the structure of the present invention obturator with the shaft means including a substantially flat strip member forming hinged portions and a plurality of segments perpendicular to the strip member and alternating with hinged portions, is substantially resistant to compression forces, which typically in mealable wire-type stylets/obturators, allow the obturator tip member to push back towards the inside of the cannula. This, in turn, complicates the intubating procedure due to the lack of a smooth transition between the obturator tip and tracheostomy tube outside diameter.

In the present invention obturator structure, the smooth transition is provided between the tip 16 and the outer diameter of the tracheostomy tube. The multi-component obturator 10 of the present invention is made as an integral single-piece, plastic device. The number of bead-like or circular disc-like segments and hinge portions is selected with respect to the length of the tracheostomy tube and the position of the curved section.

The hinge-like structure allows the obturator to be highly flexible in the axis of the tube curved section. The plurality of segments of the obturator substantially fill up the tube's interior maintaining the integrity of the tracheostomy tube, but at the same time allowing easy flexing during insertion or removal of the obturator from the tracheostomy tube. The obturator's tip is designed with a straight section which absorbs the deflection of the tube and obturator size tolerance without compromising the streamline tip profile. The handle projecting beyond the connector facilitates the withdrawal of the obturator from the tracheostomy tube.

FIGS. 7 to 10 show still another embodiment of the present invention obturator While the embodiments shown in FIGS. 1-6 can be especially advantageously used with, for example, flexible pediatric tracheostomy tubes, the obturator shown in FIGS. 7 to 10 is particularly adapted for use with adult rigid tracheostomy tubes having a curved cannula lying substantially within a given plane and having a non-constant radius.

As shown in FIGS. 7 to 10, this embodiment also includes a single-piece member 10 made of flexible material, preferably plastic, which includes a tip member 16 at the distal end 11 and grasping means 17, forming a handle at the proximal end 12. Shaft means 13 extends between the proximal and distal ends 11,12. The shaft means 13 over a substantial portion of its length is dimensioned such as to impart sufficient rigidity both in the direction substantially perpendicular and substantially parallel to the given plane of its curvature corresponding to a given plane of the cannula's curvature. The portion of the shaft means 13 having rigidity is divided into a first and second rigid sections 51 and 52.

The shaft means 13 further includes a flexible section 53 which is positioned adjacent the distal end of the obturator between substantially rigid sections 51 and 52 and includes portions 60. The first flexible section 53 (portions 60) is of a substantially rectangular cross-section and has a width and thickness, with the width as measured perpendicular to the given plane substantially exceeding the thickness. The shaft means 13 is easily flexible along its in the given plane of its curvature at the first flexible section 53, but substantially stiff in a direction perpendicular to the given plane because of the greater width of its cross-section. In this particular embodiment, the rigid sections 51 and 52 include a first flat member 54 which has a rectangular cross-section corresponding to that of the flexible section 53 and is continuous therewith and also includes a web-like member 55 which is substantially perpendicular to the width of the first member 54. In this preferred embodiment, the flexible section 53 also includes at least one protuberance 57 positioned substantially perpendicular to the width of the flexible section 53 and spaced from the first and second rigid sections 51,52. Accordingly, the obturator flexes at the spaces between the protuberance and the first and second sections. The flexible section 53 may include more protuberances spaced apart, such that the obturator would flex also at the space between the protuberances. This would be advantageous for obturators having an extended length. Also, the protuberances may have different shapes, such as, for example, circular discs, and bead-like members similar to those discussed with respect to embodiments shown in FIGS. 1-6.

The obturator is also provided with a second portion 58 which is provided behind the first flexible section 53 as seen along the length of the obturator 10 in the direction of its proximal end 12. In this embodiment, the second portion 58 is constituted by a raised fin member or second protuberance provided on the web-like member 55 of the first rigid section of the shaft means 13 and is so dimensioned that when the obturator 10 is inserted into the tracheostomy tube 100 it contacts the inner wall of the cannula 20 preventing the obturator from collapsing inside the cannula and also preventing the distal tip end of the obturator from receding into the cannula. This feature is extremely important since it prevents the tip of the obturator from being pushed up inside the tracheostomy tube while the physician is placing the tube into the patient. The provision of a flexible section within the obturator design allows the physician to withdraw the obturator from the tube without necessarily following the line of curvature of the tube.

It will be understood that variations and modifications may be effected without departing from the spirit and scope of the novel concepts of the present invention.

We claim:

1. In combination, a tracheostomy tube including a curved cannula lying substantially within a given plane and formed with a non-constant radius, and an obturator means insertable into said cannula for guiding intubation of said tracheostomy tube, said obturator means comprising:

a single piece member formed of a resilient and flexible material and curvable upon insertion within said cannula with a radius lying within said given plane, said member having a proximal and a distal end and shaft means extending therebetween, said shaft means including at least on substantially rigid portion over a substantial portion of its length being dimensioned such as to impart sufficient rigidity both in a direction substantially perpendicular and also substantially parallel to said given plane, said shaft means also including at least one flexible section, said shaft means at said flexible section having two portions of substantially rectangular cross-section having a width and a thickness, said width as measured perpendicular to said given plane substantially exceeding its thickness, and a first protuberance located between said two portions, said flexible section being positioned substantially adjacent said distal end;

said shaft means at said flexible section being easily flexible along its length in said given plane of its curvature but being substantially stiff in a direction perpendicular to said given plane because of the greater width of its cross-section at said two portions;

said shaft also including a second protuberance having a diameter larger than that of the first protuberance.

2. An obturator according to claim 1, wherein said second protuberance is a raised fin member located behind said flexible section, as seen along the length of said shaft means in the direction towards its proximal end, said fin member having its diameter exceeding the diameter of said first protuberance and of the remaining portions of said shaft means, said diameter of said second section corresponding to the inner diameter of said cannula, wherein upon insertion of said obturator into said cannula, said raised fin member contacts an inner wall of said cannula and prevents backward movement of said obturator in said cannula.

3. An obturator according to claim 2, wherein said substantially rigid portion of said shaft means is divided into a first and second rigid section separated by said flexible section.

4. An obturator according to claim 3, wherein said first and second rigid sections include a first flat member having a cross-section corresponding to that of said flexible section and being continuous therewith and also include a web portion substantially perpendicular to the width of said flat member.

5. An obturator according to claim 4, wherein said raised fin member is provided on said web portion of said first rigid section.

6. In combination, a tracheostomy tube including a curved cannula lying substantially within a given plane and formed with a non-constant radius, and an obturator means insertable into said cannula for guiding intubation of said tracheostomy tube, said obturator means comprising:

a single piece member formed of a resilient and flexible material and curvable upon insertion within said cannula with a radius lying within said given plane, said member having a proximal and a distal end and shaft means extending therebetween, said shaft means including at least one substantially rigid portion over a substantial portion of its length being dimensioned such as to impart sufficient rigidity both in a direction substantially perpendicular and also substantially parallel to said given plane, said shaft means also including a single flexible section, said shaft means at said flexible section having two portions of substantially rectangular cross-section having a width and a thickness, said width as measured perpendicular to said given plane substantially exceeding its thickness, said two portions being positioned apart from each other and along said shaft, and a single protuberance located between said two portions, said flexible section being positioned substantially adjacent said distal end, the thickness of said two portions being also substantially less than the thickness of all the remaining portions of said shaft means;

said shaft means at said flexible section being easily flexible along its length at said two portions in said given plane of its curvature but being substantially stiff in a direction perpendicular to said given plane because of the greater width of its cross-section at said two portions.

* * * * *